(12) United States Patent
Morris

(10) Patent No.: US 7,093,481 B2
(45) Date of Patent: Aug. 22, 2006

(54) METHOD FOR ROLLER BURNISHING A HEATER TUBE

(76) Inventor: David L. Morris, P.O. Box 12412, San Antonio, TX (US) 78212-0412

( * ) Notice: Subject to any disclaimer, the term of this patent is extended or adjusted under 35 U.S.C. 154(b) by 0 days.

(21) Appl. No.: 10/986,706

(22) Filed: Nov. 12, 2004

(65) Prior Publication Data
US 2005/0067413 A1 Mar. 31, 2005

Related U.S. Application Data

(63) Continuation-in-part of application No. 09/943,189, filed on Aug. 30, 2001, now abandoned.

(60) Provisional application No. 60/229,624, filed on Aug. 31, 2000.

(51) Int. Cl.
G01N 33/22 (2006.01)
B24B 39/00 (2006.01)

(52) U.S. Cl. ............. 73/61.62; 29/90.01; 72/112; 72/122

(58) Field of Classification Search .......... 29/90.01, 29/90.2, 90.3, 90.5; 72/95, 112, 115, 117, 72/118, 122; 73/35.02, 61.41, 61.62; 409/4
See application file for complete search history.

(56) References Cited

U.S. PATENT DOCUMENTS

| | | | |
|---|---|---|---|
| 3,670,561 A | 6/1972 | Hundere | |
| 5,101,658 A | 4/1992 | Wilson, III et al. | |
| 5,337,599 A | 8/1994 | Hundere et al. | |
| 5,540,883 A * | 7/1996 | Jones et al. | 419/28 |

OTHER PUBLICATIONS

"Burnishing Tools and Machines"to Cogsdill Tool Products, 2002, pp. 1-58.*
"Robuto Roller Burnishing Tools"to Yamato, 2003, pp. 1-25.*
"Bright Burnishing Tools"to Bright, 2004, pp. 1-20.*

* cited by examiner

Primary Examiner—Hezron Williams
Assistant Examiner—David A. Rogers
(74) Attorney, Agent, or Firm—Strasburger & Price, LLP; Alan R. Thiele

(57) ABSTRACT

A process for placing a roller burnished finish on the central portion of an unfinished lathe-turned heater tube includes controlling the rotational speed of the burnishing rollers and the pressure of the burnishing rollers against the central portion of the heater tube so that tooling marks are no longer apparent under substantially 10× magnification and the length of the central portion of the heater tube increases by no more than 0.002 inches per inch of length of the central portion of the heater tube.

3 Claims, 4 Drawing Sheets

METHOD FOR ROLLER BURNISHING A HEATER TUBE

This application is based upon U.S. Provisional Patent Application Ser. No. 60/229,624 filed Aug. 31, 2000, entitled "Heater Tube" and is a Continuation-in-Part of U.S. patent application Ser. No. 09/943,189 filed Aug. 30, 2001 entitled "Heater Tube," now abandoned.

FIELD

This invention relates generally to a method for making a heater tube used in the measurement of the thermal oxidation properties of jet fuel; more particularly this invention relates to a process for roller burnishing the outside surface of the central portion of a heater tube.

BACKGROUND

In the early 1970s, the American Society for Testing and Materials™ (ASTM) promulgated ASTM D3241 Standard Test Method for Thermal Oxidation Stability of Aviation Turbine Fuels Procedure. This published ASTM standard, most recently revised in 2004, is incorporated herein by reference. The test described in ASTM D3241 measures the thermal stability of jet fuel by subjecting it to test conditions simulating those occurring in jet engine fuel systems.

The ASTM D3241 standard describes the use of an apparatus that, over a period of 2.5 hours, pumps 450 mL of pressurized jet fuel at a fixed volumetric flow rate around and over a single-use long, thin, cylindrical, heated aluminum tube. Such single-use tubes are typically referred to as heater tubes. The color and other characteristics of any fuel oxidation products (i.e., deposits) left on the surface of the central portion of the heater tube, are then evaluated to assess the thermal stability of the jet fuel being tested.

The quality of the surface finish of the single-use heater tube used in the ASTM D3241 test is key to obtaining satisfactory test results. U.S. Pat. No. 3,670,561 ("the '561 patent"), issued Jun. 20, 1972, to Alf Hundere, and which is incorporated herein by reference, illustrates a typical heater tube.

The heater tube used to test jet fuels has a generally circular cross-sectional shape, a substantially constant internal diameter, and an outside diameter that is larger at its extremities than at its central portion. The '561 patent suggests that the heater tube be constructed of aluminum, to minimize manufacturing cost. The outer diameter of the central portion of the tube may be as small as $1/8^{th}$ of an inch. Furthermore, the '561 patent indicates that the heater tube should have a highly polished surface finish that is consistent from tube to tube and is suitable for rating the level of fuel deposited thereon during a test. U.S. Pat. No. 5,101,658 ("the '658 patent") and U.S. Pat. No. 5,337,599 ("the '599 patent") similarly depict and describe a heater tube and are also incorporated herein by reference.

A paper entitled "Comparison of JFTOT Heater Tube Deposit Rating Methods for the Evaluation of Fuel Thermal Stability," by Robert Morris, et al. of the Naval Research Laboratory, published Dec. 29, 1987, discloses that a standard heater tube can be manufactured from a common aluminum alloy known as 6061-T6 aluminum. 6061-T6 aluminum is an extremely popular alloy because of its low cost, good formability, corrosion resistance, high strength, and attractive appearance.

Disposable heater tubes for testing the thermal stability of fuels have been in existence for more than 30 years. A typical finished heater tube is approximately $6\frac{3}{8}$ inches in length, including an approximately $2\frac{3}{8}$ inch central portion. The central portion of the heater tube has an outer diameter of approximately $1/8$ inch. The remainder of the heater tube has an outer diameter of approximately $3/16$ inch.

While the ASTM D3241 standard and the '561, '658, and '599 patents disclose various aspects of the heater tube and the need for a consistent, "highly polished" surface finish, these references do not describe a means, a method, or a best process for obtaining the consistent "highly polished" surface finish. A SAE Technical Paper presented at the Aerospace Technology Conference & Exposition at Long Beach, Calif., between Oct. 14 and 17, 1985, by G. Datschefski and T. G. R. Farthing, entitled "Evaluation of JFTOT Tube Deposits by Carbon Burnoff" indicates that the industry's standard method of creating the surface finish on heather tubes is by the use of a petroleum distillate-based metal polishing liquid containing ammonia.

A metal polishing liquid typically includes an abrasive material suspended in wet lapping. The abrasive material in the metal polishing liquid cuts tiny grooves into the surface of the workpiece being polished. Because these tiny grooves are so small, when a metal polishing liquid is used on a heater tube, the surface of the heater tube appears to the human eye as being bright, reflective, and shiny. Interestingly, the more numerous these tiny grooves, the brighter, shinier and more reflective the surface finish of the heater tube is to the human eye. However, brightness, shininess and reflectivity does not equate to a good surface finish for a heater tube that is used in a jet fuel stability test.

The ASTM D3241 standard test method calls for a visual inspection of the heater tube prior to use. Such visual inspection typically includes checking the surface finish for quality defects and other inconsistencies under a magnifier.

It has long been desired to produce a heater tube with a surface finish superior to that which could be obtained by conventional polishing techniques. Such a heater tube having a superior surface finish would permit advances in studies to understand the mechanism of jet fuel deposit formation on the surface of the central portion of aluminum heater tubes. Use of a heater tube with a superior surface finish would result in a reduction in light scattering from the surface of the heater tube. The reduction in light scattering would permit improved visual observation and study of fuel deposits and their resultant fuel-related effects by reducing the glare associated with heater tubes whose surface finish has been created by the use of abrasive liquid polishing techniques. A heater tube with a superior surface finish would also permit advances in prior art deposit measurement techniques and the development or successful application of new deposit measurement protocols and techniques such as ellipsometry.

One of the techniques that has been evaluated for obtaining a superior surface finish on the central portion of a heater tube is roller burnishing. While roller burnishing has long been practiced as a way of achieving an improved visually pleasing finish on the surface of different items, to include cylindrical workpieces made from aluminum, prior art roller burnishing techniques failed when applied to heater tubes. Specifically, prior art roller burnishing techniques did not produce consistent, high quality surface finishes. For example, in the instruction manual for the CX-1T External Roller Burnishing Machine (copyright 1992), Cogsdill Tool Products, Inc. of Lugoff, S.C., it is indicated that the smaller the workpiece, the greater the speed needed for the roller burnishing tool to obtain a satisfactory surface finish. When this prior art technique of increasing the speed of the roller burnishing tool was tried on aluminum heater tubes, unsatisfactory surface finish results were obtained. Not only is the prior art incorrect with regard to the speed of the roller burnishing tool, but the prior art on roller burnishing also does not provide any instruction concerning the force to be placed on the surface of the heater tube by the burnishing rollers. Nor does the prior art provide any instruction as to understanding when the surface of the workpiece is to be considered as being roller burnished to an acceptable surface finish.

Therefore, there remains a need in the art for a roller burnishing method that will burnish the surface finish of a heater tube.

SUMMARY

The present invention provides a process for reliably roller burnishing the surface of the central portion of a heater tube using a roller burnishing machine having three tapered burnishing rollers driven by a rotating mandrel. The three tapered burnishing rollers are in contact with the surface of the central portion of an unfinished lathe-turned heater tube.

The force on the three tapered burnishing rollers which contact the heater tube is provided by the rotating mandrel. The rotating mandrel bears against those sides of the three tapered burnishing rollers that are away from the heater tube being finished. The three tapered burnishing rollers are drawn inwardly against the outer surface of the central portion of the heater tube to provide a steady rolling pressure. The steady rolling pressure and the speed of the rotating mandrel is set so that the characteristics of a properly roller burnished heater tube fall between two observable parameters. The first observable parameter is the absence of tooling marks on the central portion of the unfinished heater tube under substantially 10× magnification. The tooling marks on an unfinished heater tube result from using a lathe to make the heater tube; specifically, the tooling marks appear under substantially 10× magnification as ridges, striations, peaks and valleys. The second observable parameter is the length of the central portion of the heater tube. According to the present invention, a properly executed process for burnishing the central portion of a heater tube results in a finished heater tube where the tooling marks on the central portion of the heater tube are no longer visible under a substantially 10× magnification and the overall length of the central portion of the heater tube increases by no more than about 0.002 inch per inch of length of the central portion of the heater tube.

DETAILED DESCRIPTION

Figure 1:
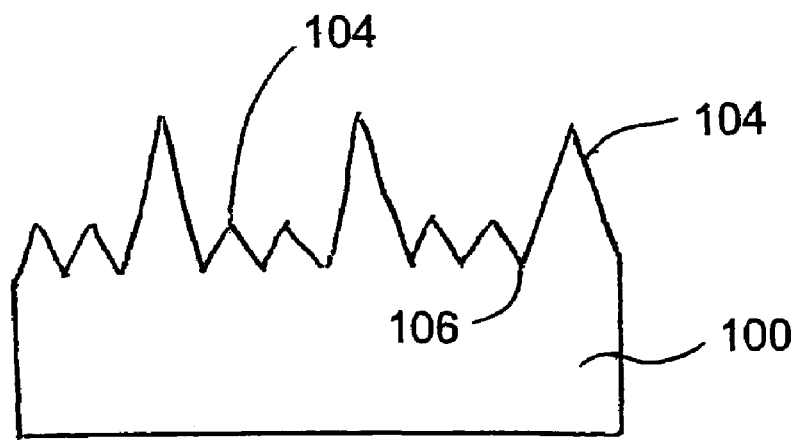
FIG. 1 is a microscopic side view illustration of the center portion of an unfinished lathe-turned heater tube showing a pattern of tooling marks.

FIG. 1 shows a representation of the surface finish of an unfinished lathe-turned heater tube 100. The surface finish is characterized by a regular pattern of ridges and peaks 104 and valleys and striations 106. These ridges and peaks 104, together with the valleys and striations 106, are the tooling marks which remain after turning the heater tube 100 on a lathe.

Figure 2:
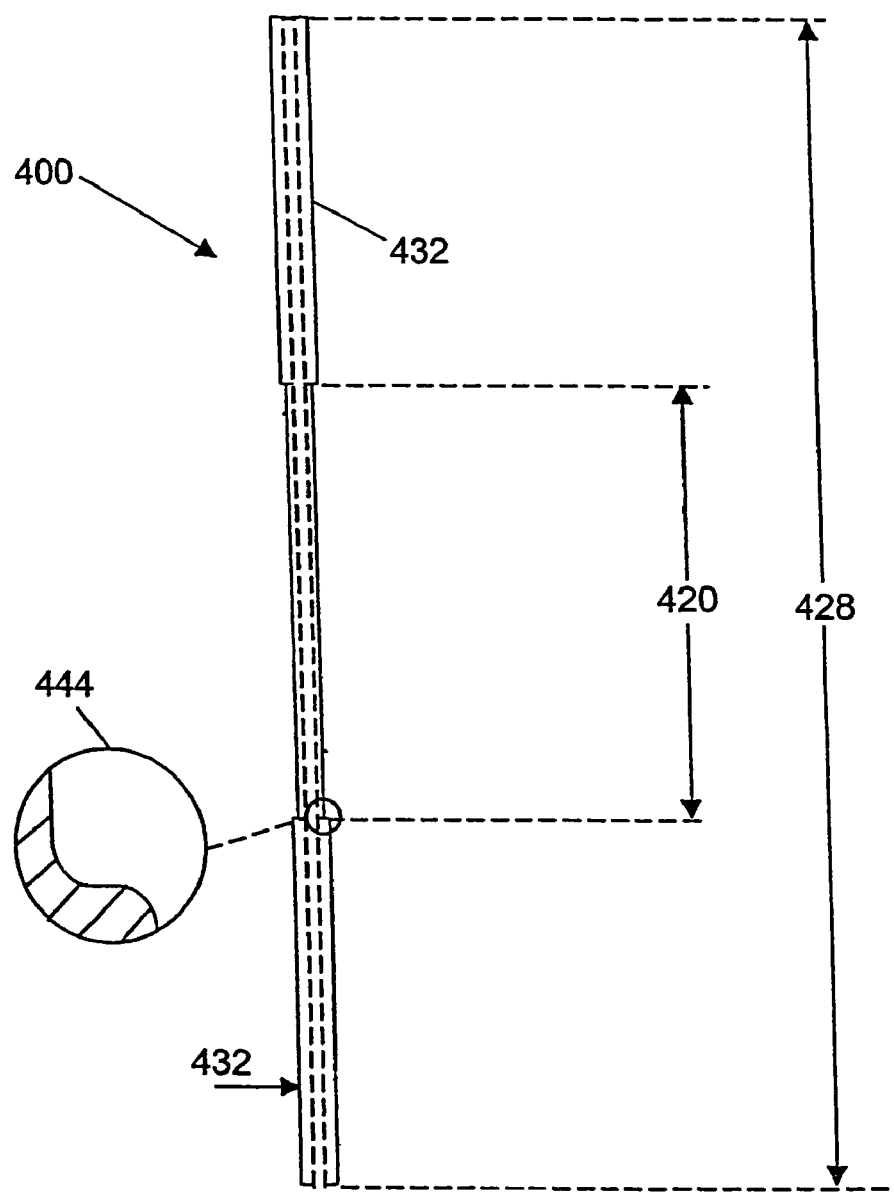
FIG. 2 is a side view of a typical heater tube for use in a fuel testing apparatus.

FIG. 2 is a side view of a heater tube 400 having an overall length 428, a central portion 420, and end portions 432. There is a shoulder area 444 between the central portion 420 and the end portions 432.

The ASTM D3241 standard test method requires that the heater tube be made of an aluminum alloy containing magnesium. 6061-T6 aluminum describes an aluminum alloy that contains magnesium and is used most often for heater tubes because it possesses an attractive appearance and is an inexpensive, heat-treatable aluminum alloy having good formability and corrosion resistance with high strength.

The aluminum heater tube whose surface finish is the object of the present invention is manufactured on a lathe from seamless aluminum tubing. In a commonly used embodiment, the outer diameter of the central 2⅜-inch portion of a 6⅜-inch long heater tube is approximately ⅛ inch, and the outer diameters of the end portions are approximately 3/16 inch.

Figure 3:
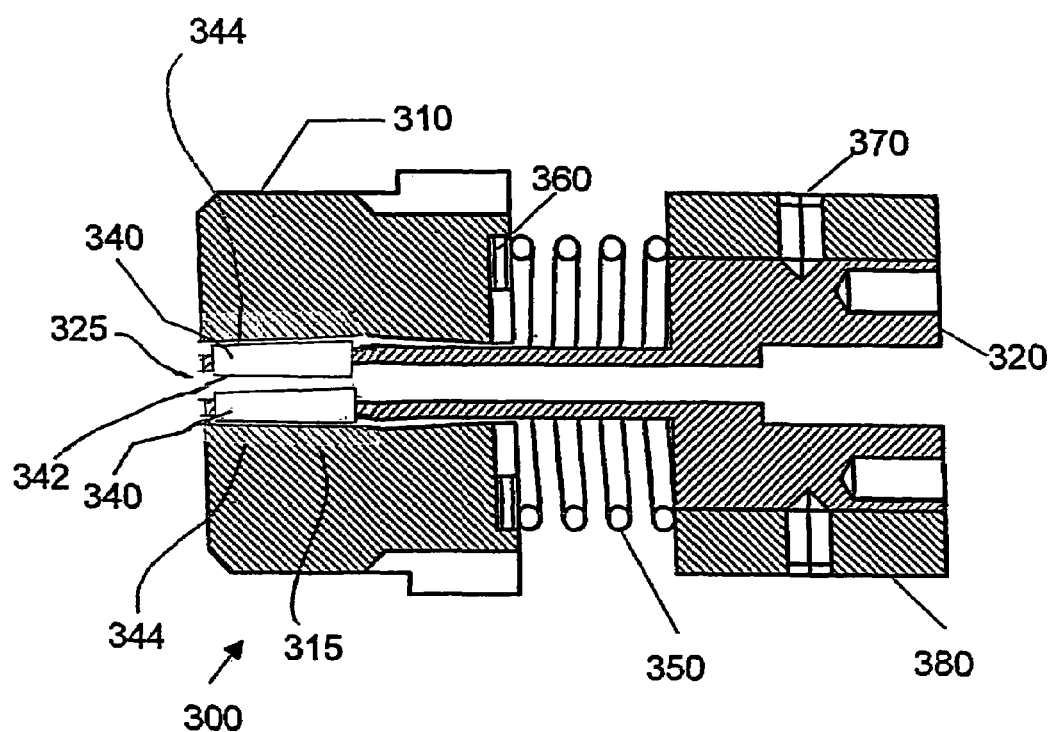
FIG. 3 is a side view of a cross section of a portion of a burnishing machine for burnishing a heater tube in accordance with the present invention.

FIG. 3 is a side view of a cross section of a roller burnishing machine assembly 300 for roller burnishing the surface finish of a heater tube in accordance with the present invention. The inner surfaces 342 of three equally-spaced, identical, hardened, highly-finished, precision-tapered, steel burnishing rollers 340 are positioned to roll around the central portion of the heater tube by having their outside surfaces 344 bear against an inversely tapered rotating mandrel 310. The inversely tapered rotating mandrel 310 is positioned to apply steady rolling pressure against the outside surface 344 of each burnishing roller 340. The pressure on the outside surface 344 of each burnishing roller 340 becomes the pressure applied to the surface of an unfinished lathe-turned heater tube that is slowly inserted into an opening 325 between the burnishing rollers 340. The three burnishing rollers 340 are held in place by a removable cage 320. A cage retainer 380 retains the removable cage 320 by means of set screws 370. A spring 350 connects the cage 320 and cage retainer 380 to the rotating mandrel 310 by means of thrust race and bearings 360. Furthermore, an air pressure mechanism (not shown) causes the cage 320 and rollers 340 to advance and retract within and along the cylindrical axis of the rotating mandrel 310. Because of the taper of the surface of the rotating mandrel which contacts the outside surfaces 344 of the burnishing rollers 340 the advancement of the tapered rotating mandrel 310 (to the right in FIG. 3) increases the force applied by the burnishing rollers 340 on the central portion of the heater tube being roller burnished.

When a roller burnishing machine 300 is used to roller burnish a metal cylindrical workpiece, the workpiece is inserted into the aperture 325 between the burnishing rollers 340 at the center of the rotating mandrel 310. As the rotating mandrel 310 rotates against the outside surface 344 of the burnishing rollers 340, the rotational movement of the mandrel 310 and the frictional contact between the rotating mandrel 310 and the outside surface 344 of the burnishing rollers 340 causes the burnishing rollers 340 to rotate in the opposite direction from the rotating mandrel 310. The tapered surface 315 of the internal portion of the rotating mandrel 310 forces the burnishing rollers 340 inwardly against the outer surface of the unfinished heater tube. The disclosed roller burnishing process produces a mirror-like surface on the central portion of the heater tube.

Figure 4:
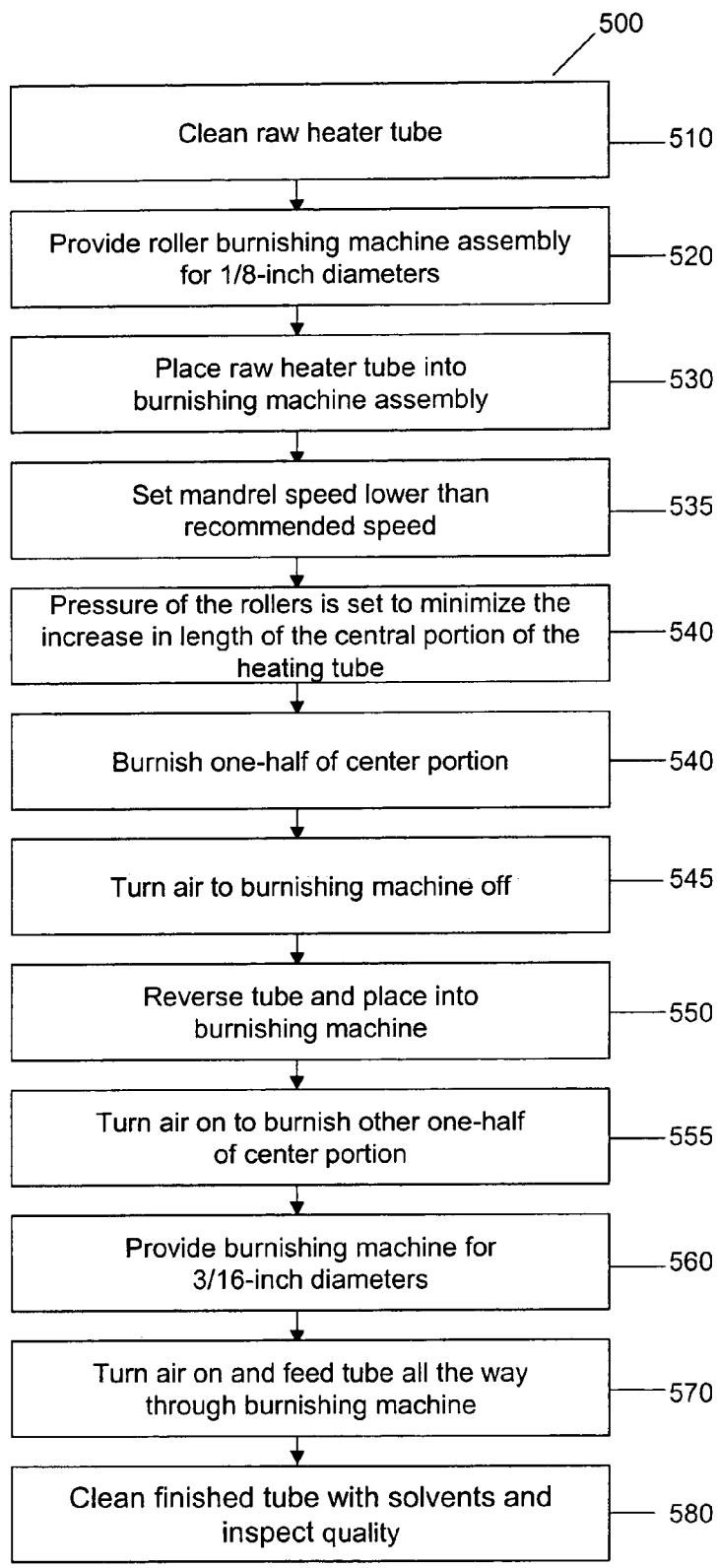
FIG. 4 is a flow diagram of one embodiment of a process for burnishing a raw heater tube, utilizing the burnishing machine of FIG. 3.

FIG. 4 is a flow diagram of the preferred embodiment of process 500 for roller burnishing an unfinished heater tube.

In step 510, a blank or raw unfinished lathe-turned heater tube is cleaned with a suitable cleaning agent or solvent such as hexane, or by other suitable cleaning processes, to remove any dirt or debris. Dirt or debris should be removed to avoid having it ground into the surface of the heater tube by the roller burnishing machine 300.

In step 520, a conventional roller burnishing machine assembly 300 (FIG. 3) is provided for burnishing the central portion 420 (FIG. 2) of the unfinished, lathe-turned heater tube 200.

In step 530, the unfinished, lathe-turned heater tube is placed part way into the aperture 325 (FIG. 3.) of the roller burnishing machine assembly 300. In step 540, the tube is roller burnished from about the center of the tube to about the shoulder 444 (FIG. 2) of the tube. The pressure or force on the central portion of the unfinished heater tube is set so that no tooling marks from the lathe-turning process are visible using a viewer having substantially 10× magnification after the roller burnishing process is completed. If insufficient pressure is applied to the heater tube by the burnishing rollers, tooling marks will still be visible. If too much pressure is applied to the central portion of the heater tube by the burnishing rollers, the overall length of the heater tube will increase, or the quality of the surface finish will decrease. In actual testing, pit marks have been observed in the surface finish of the central portion of the heater tube when too much pressure is applied during the roller burnishing process. Any increase in length of the central portion heater tube beyond about 0.002 inches per inch of length of the central portion of the heater tube is unacceptable. Thus, for an unfinished heater tube having a central portion whose length is 2.375 inches, any increase in the length of the central portion beyond 0.005 inches would be unacceptable (2.375×0.002≅0.005). It is also important that variations in the pressure of the burnishing rollers against the surface of the central portion of the unfinished heater tube be tightly controlled to assure uniformity in the quality of the surface finish.

It has also been found that the rotating mandrel 310 should be maintained at a speed of approximately 140 rotations per minute (RPM). While approximately 140 RPM is the preferred rotational speed of the rotating mandrel, any rotational speed between about 50 RPM and about 300 RPM will not detract from the operability of the disclosed method. This rotational speed for the rotating mandrel 310 is substantially slower than recommended by roller burnishing machine manufacturers for workpieces as small as the heater tubes described herein.

Because the diameter of the burnishing rollers 340 is smaller than the inner diameter of the rotating mandrel 310, the burnishing rollers 340 rotate faster than the rotating mandrel 310, and in the opposite spin direction. In the preferred embodiment, operating the rotating mandrel at speeds of approximately 50 to approximately 300 RPM results in burnishing roller speeds of approximately 125 RPM to approximately 750 RPM. As will be understood by those of ordinary skill in the art, the heater tube 400 itself, whose diameter (at the central portion 420) is even smaller than the diameter of the burnishing rollers 340, rotates at even higher speeds, between approximately 200 RPM and approximately 1200 RPM. A rotational speed of between approximately 50 RPM to approximately 300 RPM for the rotating mandrel 310 is far below the 2000 RPM typically recommended by roller burnishing machine manufacturers for small diameter workpieces.

In step 545, the air to the roller burnishing machine assembly 300 is turned off. This releases the pressure of the rotating mandrel 310 on the burnishing rollers 340. In step 550, the tube is removed, reversed, and replaced into the aperture 325. In step 555, air to the roller burnishing machine assembly 300 is turned on again so that the pressure of the burnishing rollers is the same as it was in step 540. The heater tube is then roller burnished outwardly from its center.

In optional steps 560 and 570, the roller burnishing machine assembly 300 may be used to roller burnish the end portions of the heater tube.

In step 580, the roller burnished heater tube 200 is cleaned, using an appropriate cleaner or solvent, to remove any lubricant, dirt, or other residue. The roller burnished heater tube is also inspected to assure that the process has resulted in an acceptable surface finish.

While the disclosed invention has been illustrated and described according to its preferred embodiment, it will be apparent to those of ordinary skill in the art that many more embodiments and implementations are possible within the scope of this invention. Accordingly, the invention is not to be restricted except in light of the attached claims.

I claim:

1. A method of roller burnishing out the tooling marks on the central portion of a lathe-turned heater tube blank for use in a machine for testing fuel quality, said method of roller burnishing being applied to a roller burnishing machine having three tapered rollers equally spaced around the central portion of the lathe-turned heater tube blank having tooling marks thereon and driven by a rotating mandrel, said method of roller burnishing out the tooling marks from the central portion of the lathe-turned heater tube blank comprising the steps of:

setting the pressure of the three burnishing rollers on the central portion of the lathe-turned heater tube blank so that the overall length of the finished heater tube has increased by no more than about 0.002 inches per inch of length of the central portion of the heater tube; and setting the speed of the burnishing rollers with respect to the lathe-turned surface of the central portion of the heater tube blank so that no tooling marks are visible with a magnification of the surface finish of substantially ten times.

2. The method as defined in claim 1 wherein the rotational speed of the rotating mandrel used to roller burnish the central portion of a lathe turned heater tube blank having a ⅛ inch diameter is between about 50 RPM and about 300 RPM.

3. A process for eliminating tooling marks on the central portion of an unfinished lathe-turned heater tube blank wherein said elimination of tooling marks will enable use of the heater tube blank in a fuel testing machine, said process comprising the steps of:

inserting the unfinished lathe-turned heater tube blank into a burnishing machine having three tapered burnishing rollers in contact with the lathe-turned surface of the central portion of the heater tube blank;

setting the pressure of said three tapered burnishing rollers with respect to the lathe-turned surface of the central portion of the heater tube blank so that the overall length of the heater tube after roller burnishing has increased by no more than about 0.002 inches per inch of length of the central portion of the heater tube;

setting the speed for said three tapered burnishing rollers with respect to the lathe-turned surface of the central portion of the heater tube blank so that when the burnishing process is completed the tooling marks from the lathe turning will no longer be visible under a magnification of substantially 10×.

* * * * *